(12) United States Patent
Hyeon et al.

(10) Patent No.: US 9,765,187 B2
(45) Date of Patent: *Sep. 19, 2017

(54) MRI CONTRASTING AGENT FOR CONTRASTING CANCER CELL

(71) Applicants: SNU R&DB FOUNDATION, Seoul (KR); Institute for Basic Science, Daejeon (KR); The Catholic University of Korea Industry-Academic Cooperation Foundation, Seoul (KR)

(72) Inventors: Taeghwan Hyeon, Seoul (KR); Kun Na, Gyeonggi-do (KR); Daishun Ling, Seoul (KR); Wooram Park, Gyeonggi-do (KR); Byung Hyo Kim, Seoul (KR); Hyeona Yim, Gyeonggi-do (KR); Kyoung Sub Kim, Incheon (KR); Michael J. Hackett, West Chester, OH (US); Sin-jung Park, Seoul (KR); Yang Lu, Hefei (KR); Yong Sun Jeon, Incheon (KR)

(73) Assignees: SNR R&DB FOUNDATION (KR); INSTITUTE FOR BASIC SCIENCE (KR); THE CATHOLIC UNIVERSITY OF KOREA INDUSTRY-ACADEMIC (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/670,805

(22) Filed: Mar. 27, 2015

(65) Prior Publication Data

US 2016/0089455 A1 Mar. 31, 2016

(30) Foreign Application Priority Data

Sep. 26, 2014 (KR) ........................ 10-2014-0129020

(51) Int. Cl.
*A61K 49/06* (2006.01)
*C08G 69/08* (2006.01)
(Continued)

(52) U.S. Cl.
CPC .......... *C08G 69/40* (2013.01); *A61K 49/1857* (2013.01); *C08G 81/00* (2013.01); *C08G 69/08* (2013.01)

(58) Field of Classification Search
None
See application file for complete search history.

(56) References Cited

U.S. PATENT DOCUMENTS

2005/0070721 A1* 3/2005 Bae ...................... A61K 9/0019
548/339.1
2005/0118252 A1* 6/2005 Bae ...................... A61K 9/1075
424/450

(Continued)

OTHER PUBLICATIONS

Multifunctional Tumor pH Sensitive Sel-Assembled Nanoparticles for Bimodal Imaging and Treatment of Resistant Heterogeneous Tumors, Ling et al., JACS, Apr. 1, 2014, pp. 5647-5655.*

(Continued)

*Primary Examiner* — Peter A Salamon
(74) *Attorney, Agent, or Firm* — Dergosits & Noah LLP; Todd A. Noah

(57) ABSTRACT

The present invention relates to MRI contrasting agent for contrasting cancer cell which contains ultrafine nanoparticles. More particularly, the present invention is directed to a self-assembled ligand composition comprising a ligand A, which is separated at a specific pH range, and a ligand B of which surface charge changes at a specific pH range, MRI contrast agent for contrasting cancer cell comprising said ligand composition and MRI contrasting nanoparticles, and the methods for preparing them.

1 Claim, 22 Drawing Sheets
(19 of 22 Drawing Sheet(s) Filed in Color)

US 9,765,187 B2
Page 2

(51) Int. Cl.
*C08G 69/40* (2006.01)
*C08G 81/00* (2006.01)
*A61K 49/18* (2006.01)

(56) References Cited

U.S. PATENT DOCUMENTS

| | | | | |
|---|---|---|---|---|
| 2005/0186263 A1* | 8/2005 | Bae | ........................ | A61K 9/0019 424/450 |
| 2008/0300296 A1* | 12/2008 | Shin | ........................ | A61L 31/10 514/449 |
| 2012/0114564 A1* | 5/2012 | Hyeon | .................... | A61K 49/08 424/9.322 |
| 2013/0323182 A1* | 12/2013 | Hyeon | .................. | A61K 49/186 424/9.322 |
| 2014/0023594 A1* | 1/2014 | Park | .................... | A61K 49/1857 424/9.322 |
| 2016/0089436 A1* | 3/2016 | Hyeon | ................ | A61K 49/0036 424/9.32 |

OTHER PUBLICATIONS 14670805-520465 STIC search, Sep. 2016.*

* cited by examiner

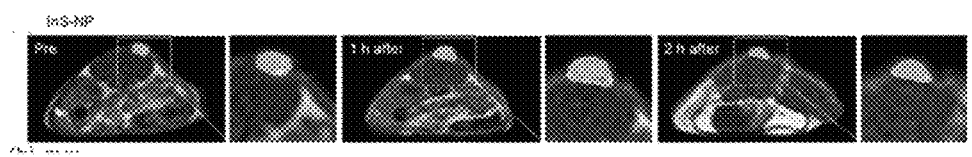
Figure 12a
Figure 12b
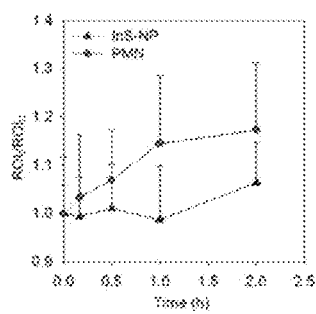 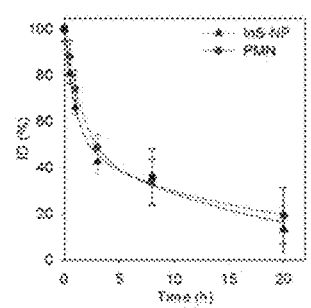 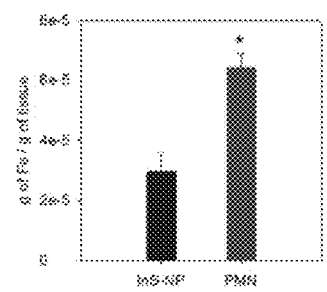
Figure 12c　　　　　　　　Figure 12d　　　　　　　　Figure 12e

MRI CONTRASTING AGENT FOR CONTRASTING CANCER CELL

CLAIM OF PRIORITY

This application claims the benefit of Korean Patent Application No. 10-2014-0129020, filed Sep. 26, 2014, the entire contents of which are incorporated herein by reference.

FIELD OF THE INVENTION

The present invention relates to MRI contrasting agent for contrasting cancer cell which contains ultrafine nanoparticles. More particularly, the present invention is directed to a self-assembled ligand composition comprising a ligand A, which is separated at a specific pH range, and a ligand B of which surface charge changes at a specific pH range, MRI contrast agent for contrasting cancer cell comprising said ligand composition and MRI contrasting nanoparticles, and the methods for preparing them.

BACKGROUND OF THE INVENTION

An important matter to consider when administering an effective drug for the treatment of a disease or the diagnosis of the disease region to a human body is how much of the administered effective ingredient reaches the disease region, that is, the problem of drug delivery efficiency. The effective ingredient may reach an unwanted normal tissue and act to cause side effects, and the amount of drug that reaches the disease region may decrease, resulting in the failure of treatment.

The drugs that have treatment effects for some diseases show strong toxicity to normal tissues or cells and, therefore, they pose problems of which their side effects or cell toxicity are greater than the treatment effect for the disease. Anticancer drugs act on normal tissue cells and have adverse effect on normal tissue cells, rather than removing cancer tissues or having treatment effect.

A cancer is caused by uncontrolled growth of cells (neoplasia) and there are over 100 cancer types. Abnormal growth of cells creates a mass of cells (tumor), and this mass of cells penetrates surrounding tissues and spreads to other parts of the body (metastasis).

Particularly, due to heterogeneity, that traces and administers drugs by using the affinity the phenomenon that cancer tissue cells produce various type of replicated tumor cells, it is difficult to utilize a method that traces cancer cells and administers drugs by using the affinity between the receptor of cancer cells and the nanoformulated ligands, which is frequently used for nanoformulated drugs. Thus, it is difficult to treat cancers by using the nanoformulated drugs.

Furthermore, such heterogeneous extracellular matrix of cancer tissues impedes drug penetration which reduces drug exposure and gradually induces drug-resistance. The cancer tissues having these characteristics are difficult to be treated by targeted therapy using antibody markers due to the heterogeneity of cancer cells.

Tumors in patients generally contain heterogeneous cell populations, and tumor heterogeneity greatly influences the effectiveness of the receptor-ligand targeting strategies that are most popularly used in cancer nanotechnology. In addition, the heterogeneous tumoral extracellular matrix impedes drug penetration which reduces drug exposure and gradually induces drug-resistance. The tumor microenvironment exhibits an increased interstitial fluid pressure caused by leaky vasculature, poor lymphatic drainage, and a high density of cells and their related matrices.

Therefore, the penetration of nanoparticle-based drugs is limited to the tumor peripheral region with little diffusion of therapeutic nanoparticles into the tumor interstitial space. The physiological and physical mechanism of drug resistance as a whole is a major cause of the failure of most cancer treatments. Although nanoparticles of small size and multi-functionality are emerging as the next-generation anti-cancer agents, there remain great challenges to the development of 'smart' nanoparticles that can specifically respond to tumor-related stimuli in order to overcome the aforementioned tumoral barriers.

Self-assembly provides a simple, reproducible and inexpensive way of producing ensembles of nanoparticles with unique plasmonic, photoluminescent, and magnetic properties in a controllable manner. Several stimulus-responsive assembled nanostructures have been thoroughly examined as bio- or chemo-sensors in vitro (Rosi, N. L.; Mirkin, C. A. Chem. Rev. 2005, 105, 1547; Cao, Y. C.; Jin, R.; Mirkin, C. A. Science 2002, 297, 1536; Zagorovsky, K.; Chan, W. C. W. Angew. Chem., Int. Ed. 2013, 52, 3168; Taton, T. A.; Mirkin, C. A.; Letsinger, R. L. Science 2000, 289, 1757; Pan, Y.; Du, X.; Zhao, F.; Xu, B. Chem. Soc. Rev. 2012, 41, 2912).

However, thus far, these types of "smart" ensembles have rarely been investigated in vivo owing primarily to these inherent physiological obstacles. One commonality among tumors is acidity; the microenvironment usually has a pH of ~6.8 and endo/lysosomes experience even lower pH values of 5.0-5.5.

Magnetic resonance imaging (MRI) is the most effective imaging diagnosis equipment up to date that can form images of the organs of living humans or animals in a non-invasive way in real time. MRI contrasting agent helps each tissue and blood vessel to be shown more clearly, so that more precise diagnosis is possible.

There are two types of MRI contrasting agent: $T_1$, which makes the target site brighter and $T_2$, which makes it darker. Paramagnetic gadolinium complex is widely used as $T_1$ contrasting agent, but low molecular weight of gadolinium complex makes the residence time within the blood vessel and body short, making exact diagnosis of vessel disease more difficult, and there has been a report that it may cause systemic fibrosis in a person with degraded kidney function.

Therefore, the object of the invention is to provide iron oxide nanoparticle-based MRI contrast agent for contrasting cancer tissue that is smaller than 100 nm holes on cancer tissue surface, which changes the surface charge from negative to positive upon reaching the cancer tissue; makes the access and penetration of the drug composition to cancer tissues easier; contains linker part which separates from the MRI contrast agent in the acidic condition of cancer tissues, thus making the penetration through cancer tissue selective and easier; and is biologically and metabolically more suitable to the body.

SUMMARY OF THE INVENTION

Technical Problem

The primary object of the present invention is to provide a ligand composition comprising a ligand A which is separated at a specific pH range, and a ligand B of which surface charge changes at a specific pH range.

Another object of the present invention is to provide an MRI contrasting agent composition for contrasting a cancer cell comprising a ligand A which is separated at a specific pH range, a ligand B of which surface charge changes at a specific pH range and MRI contrasting nanoparticles captured by an imidazole group of the ligand A.

Further object of the present invention is to provide a process for preparing a ligand composition, comprising: (i) preparing the ligand composition by adding to an organic solvent a mixture solution which is composed of a ligand A, which is separated at a specific pH range, and a ligand B of which surface charge changes at a specific pH range; and (ii) separating the ligand composition.

Yet another object of the present invention is to provide a process for preparing an MRI contrasting agent composition for contrasting a cancer cell, comprising: (i) preparing the ligand composition by adding to an organic solvent a mixture solution which contains a ligand A, which is separated at a specific pH range, and a ligand B of which surface charge changes at a specific pH range to an organic solvent; and (ii) mixing the ligand composition and MRI contrasting nanoparticle such that the MRI contrasting nanoparticle is to be captured by an imidazole group of the ligand B.

Technical Solution

The primary object of the present invention can be achieved by providing a ligand composition comprising a ligand A which is separated at a specific pH range, and a ligand B of which surface charge changes at a specific pH range.

The ligand A may contain PEG, imidazole group, catechol and chlorin E6(Ce6). The hydrophilicity of the PEG helps the ligand composition retain its form; the imidazole group makes the ligand composition change its form in response to pH change; the catechol bond to extremely small iron oxide nanoparticles (ESIONs); and the Ce6 emits reactive oxygen species (ROS) that destroy cancer cells when exposed to a proper light.

Furthermore, The ligand B may contain PEG, imidazole group, phenyl group and Ce6. The hydrophilicity of the PEG helps the ligand composition retain its form; the imidazole group makes the ligand composition change its form in response to pH change; the lipophilicity of the phenyl group helps the ligand composition retain its form; and the Ce6 emits reactive oxygen species (ROS) that destroy cancer cells when exposed to a proper light.

In an embodiment of the ligand composition of the present invention, the ligand A may be a compound of formula (I), as shown in FIG. 16, wherein n and m are independently 5-500. Also, the imidazole group of the formula (I) may be substituted by triazole or piperazine group.

Furthermore, in an embodiment of the ligand composition of the present invention, the ligand B may be a compound of formula (II), as shown in FIG. 17, wherein n and m are independently 5-500. Also, the imidazole group of the formula (II) may be substituted by triazole or piperazine. In addition, the phenyl group of the formula (II) may be substituted by naphthyl or indole group.

In one embodiment of the ligand composition of the present invention, the pH range at which ligand A separates or the surface charge of ligand B changes may be 4-7.2.

Another object of the present invention can be achieved by providing an MRI contrasting agent composition for contrasting a cancer cell comprising a ligand A which is separated at a specific pH range, a ligand B of which surface charge changes at a specific pH range and MRI contrasting nanoparticles captured by an imidazole group of the ligand A.

In one embodiment of the MRI contrasting agent composition for contrasting a cancer cell of the present invention, the ligand A may be a compound of formula (I), and the ligand B may be a compound of formula (II).

In one embodiment of the MRI contrasting agent composition for contrasting a cancer cell of the present invention, the MRI contrasting nanoparticle may be iron oxide nanoparticle. Also, the size of the nanoparticle may be 1 nm to 100 nm.

In one embodiment of the MRI contrasting agent composition for contrasting a cancer cell of the present invention, the pH range at which ligand A separates or the surface charge of ligand B changes may be 4-7.2.

Another object of the present invention can be achieved by providing a process for preparing ligand composition, comprising: (i) preparing the ligand composition by adding to an organic solvent a mixture solution which contains a ligand A, which is separated at a specific pH range, and a ligand B of which surface charge changes at a specific pH range; and (ii) separating the ligand composition.

In an embodiment of the process for preparing a ligand composition of the present invention, the ligand A may be a compound of the formula (I), and the ligand B may be a compound of the formula (II).

In one embodiment of the process for preparing ligand composition of the present invention, the pH range at which ligand A separates or the surface charge of ligand B changes may be 4-7.2.

In one embodiment of the process for preparing a ligand composition of the present invention, the solvent of the mixture solution may be DMSO (dimethyl sulfoxide), DMF (dimethylformamide) or THF (tetrahydrofuran). Also, the organic solvent may be chloroform, dichloromethane or 1,2-dichloroethane.

In one embodiment of the process for preparing ligand composition of the present invention, the ligand A may be produced by a method comprising: (i) preparing poly(ethylene glycol)-poly(β-benzyl-L-aspartate) (PEG-PBLA) by polymerizing β-benzyl-L-aspartate N-carboxy anhydride (BLA-NCA) in the mixture of DMF and $CH_2Cl_2$; (ii) preparing platform ligand by bonding chlorin E6 (Ce6) to the PEG-PBLA; and (iii) preparing ligand A by the aminolysis of the platform ligand using 1-(3-amynopropyle) imidazole and dopamine.

Furthermore, in an embodiment of the process for preparing ligand composition of the present invention, the ligand B may be produced by a method comprising: (i) preparing poly(ethylene glycol)-poly(β-benzyl-L-aspartate) (PEG-PBLA) by polymerizing β-benzyl-L-aspartate N-carboxy anhydride (BLA-NCA) in the mixture of DMF and $CH_2Cl_2$; (ii) preparing platform ligand by bonding chlorin E6 (Ce6) to the PEG-PBLA; and (iii) preparing ligand A by the aminolysis of the platform ligand using 1-(3-amynopropyle) imidazole and 3-phenyl-1-propylamine.

Further object of the present invention can be achieved by providing a process for preparing MRI contrasting agent for contrasting a cancer cell, comprising: (i) preparing ligand composition by adding to an organic solvent a mixture solution which contains a ligand A, which is separated at a specific pH range, and ligand B of which surface charge changes at a specific pH; and (ii) mixing the ligand composition and MRI contrasting nanoparticle such that the MRI contrasting nanoparticle is to be captured by an imidazole group of the ligand B.

In an embodiment of the process for preparing MRI contrasting agent for contrasting a cancer cell of the present invention, the ligand A may be a compound of the formula (I), and the ligand B is a compound of the formula (II).

In one embodiment of the process for preparing MRI contrasting agent for contrasting a cancer cell of the present invention, the pH range at which ligand A separates or the surface charge of ligand B changes may be 4-7.2.

In one embodiment of the process for preparing MRI contrasting agent for contrasting a cancer cell of the present invention, the solvent of the mixture solution may be DMSO (dimethyl sulfoxide), DMF (dimethylformamide) or THF (tetrahydrofuran). Also, the organic solvent may be chloroform, dichloromethane or 1,2-dichloroethane.

In one embodiment of the process for preparing MRI contrasting agent for contrasting a cancer cell of the present invention, the MRI contrasting nanoparticle may be iron oxide nanoparticle. Also, the size of the iron oxide nanoparticle may be 1 nm to 100 nm, In one embodiment of the process for preparing MRI contrasting agent for contrasting a cancer cell of the present invention, the ligand A may be produced by a method comprising: (i) preparing poly(ethylene glycol)-poly(β-benzyl-L-aspartate) (PEG-PBLA) by polymerizing β-benzyl-L-aspartate N-carboxy anhydride (BLA-NCA) in the mixture of DMF and $CH_2Cl_2$; (ii) preparing platform ligand by bonding chlorin E6 (Ce6) to the PEG-PBLA; and (iii) preparing ligand A by the aminolysis of the platform ligand using 1-(3-amynopropyle)imidazole and dopamine.

Furthermore, in one embodiment of the process for preparing MRI contrasting agent for contrasting a cancer cell of the present invention, the ligand B may be produced by a method comprising: (i) preparing poly(ethylene glycole)-poly(β-benzyl-L-aspartate) (PEG-PBLA) by polymerizing β-benzyl-L-aspartate N-carboxy anhydride (BLA-NCA) in the mixture of DMF and $CH_2Cl_2$; (ii) preparing platform ligand by bonding chlorin E6 (Ce6) to the PEG-PBLA; and (iii) preparing ligand B by the aminolysis of the platform ligand using 1-(3-amynopropyle) imidazole and 3-phenyl-1-propylamine.

Advantageous Effects

The nanoformulation of the MRI contrasting agent for contrasting a cancer cell of the present invention is a self-assembled nanostructure that reacts to the acidic stimulation of tumors and functions to carry the MRI contrasting agent selectively to cancer cells. Therefore, the nanoformulation of the MRI contrasting agent for contrasting a cancer cell of the present invention allows for an early stages diagnosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12a shows in vivo $T_1$-weighted MR images and color-mapped images of tumor sites before and 1 or 2 hours after intravenous injection of InS-NPs into nude mice bearing HCT116 tumors (the dashed regions indicate tumor site).

FIG. 12b shows in vivo $T_1$-weighted MR images and color-mapped images of tumor sites before and 1 or 2 hours after intravenous injection of PMNs into nude mice bearing HCT116 tumors (the dashed regions indicate tumor site).

FIG. 12c shows plot of signal intensity enhancement (ROE/ROIO) versus time after injection of PMNs and InS-NPs.

FIG. 12d shows blood circulation data (plasma iron concentration vs time) for PMNs and InS-NPs in nude mice (see inset; n=3 for each group).

FIG. 12e shows inductively coupled plasma atomic emission spectroscopy (ICP-AES) analysis of tumor tissue shows >2-fold increase of PMNs than InS-NPs in HCT116 tumors at 12 h after intravenous injection.

DETAILED DESCRIPTION OF THE INVENTION

Hereinafter, the present invention will be described in greater detail with reference to the following examples. The examples are given only for illustration of the present invention and not to be limiting the present invention.

Example 1. Synthesis of Ligands

Figure 18:
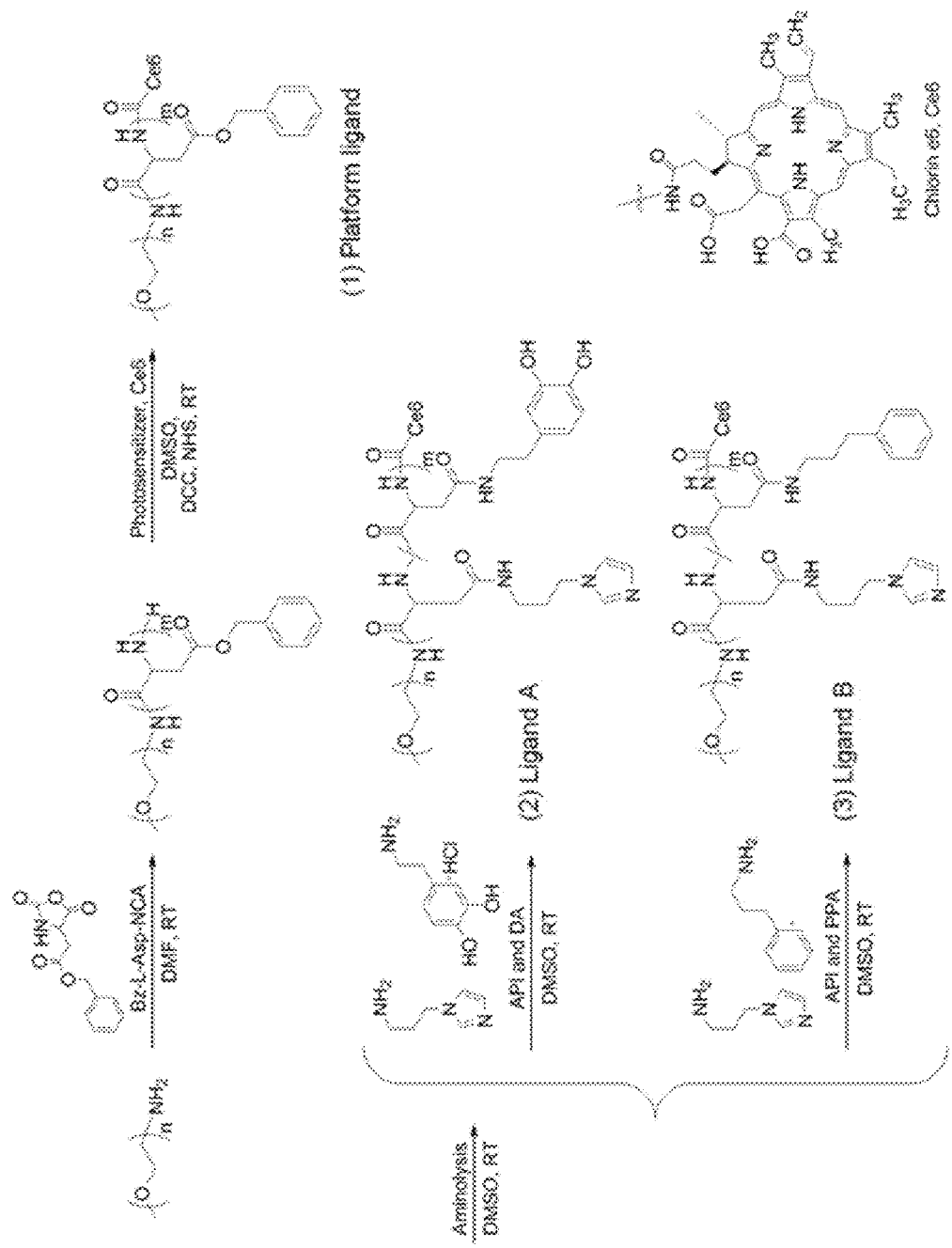
FIG. 18 shows the template for synthesis of ligands A and B.

As shown in FIG. 18, ligands A and B were synthesized by using poly(ethylene glycol)-poly(β-benzyl-L-aspartate) (PEG-PBLA) as a template.

Figure 1:
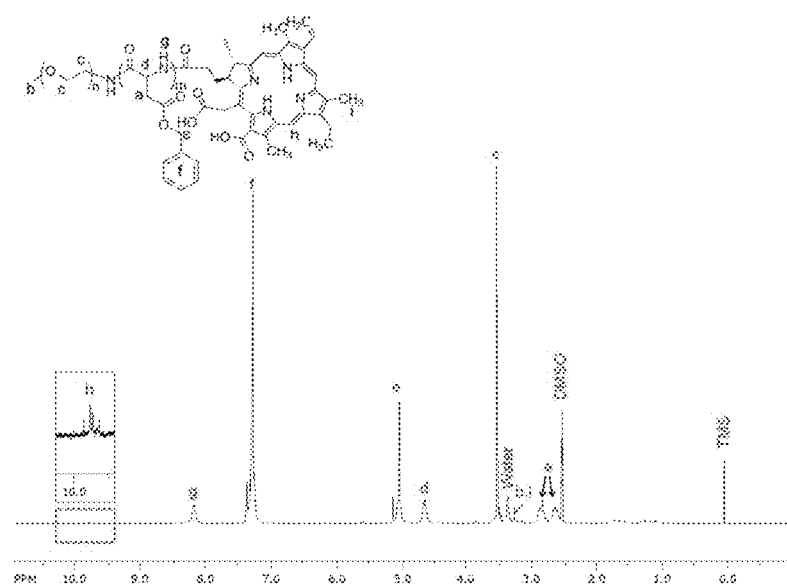
FIG. 1 shows H-NMR analysis of the platform ligand (PEG-PBLA-Ce6) synthesized in Example 1 of the present invention.

To prepare PEG-PBLA, β-Benzyl-L-aspartate N-carboxy anhydride (BLA-NCA) (3 g, 12 mmol) was polymerized in a mixture of DMF (20 mL) and $CH_2Cl_2$ (50 mL) at 40° C. by initiation from the terminal primary amino group of α-methoxy-ω-amino-poly(ethylene glycol) (MW=2,000 Da, 240 mg, 120 μmol). PEG-PBLA was purified by precipitation in ether (3 L) three times. To synthesize PEG-PBLA-Ce6 (platform ligand), Ce6 was attached to the amine groups of PEG-PBLA via the conventional carbodiimide reaction. The PEG-PBLA (0.5 g, 32.5 μmol,) and a mixture of Ce6 (23.4 mg, 39.0 μmol), dicyclohexylcarbodiimide (9.6 mg, 46.8 μmol), and N-hydroxysuccinimide (5.4 mg, 46.8 μmol) were dissolved separately in DMSO (5 mL) and the solutions were stirred thoroughly for 3 h prior to the condensation reaction. The two reactant solutions were then mixed and stirred at room temperature. After 24 h, the reaction mixture was filtered to remove the insoluble by-products (e.g., dicyclohexylurea) and dialyzed against deionized water for 2 days (Spectra/Por; molecular weight cutoff size, MWCO: 1,000 Da). The final solution was lyophilized to obtain the platform ligand. The hydrogen nuclear resonance spectroscopy ("H-NMR") analysis of the platform ligand (PEG-PBLA-Ce6) at 300 MHz with DMSO-$d_6$ is illustrated in FIG. 1, where δ=9.7 ppm (1H, s, —CH= of Ce6), 8.1 ppm (1H, s, —NH—), 7.3 ppm (5H, s, —$CH_2C_6H_5$—), 5.0 ppm (2H, —$CH_2C_6H_5$—), 4.6 ppm (1H, m, —NHC HC=O—), 3.5 ppm (182H, s, —$CH_2CH_2O$— of mPEG), 3.2 ppm (3H, s, $CH_3$— of mPEG) and 2.9-2.5 ppm (2H, m, CH$CH_2$C=O).

Figure 2:
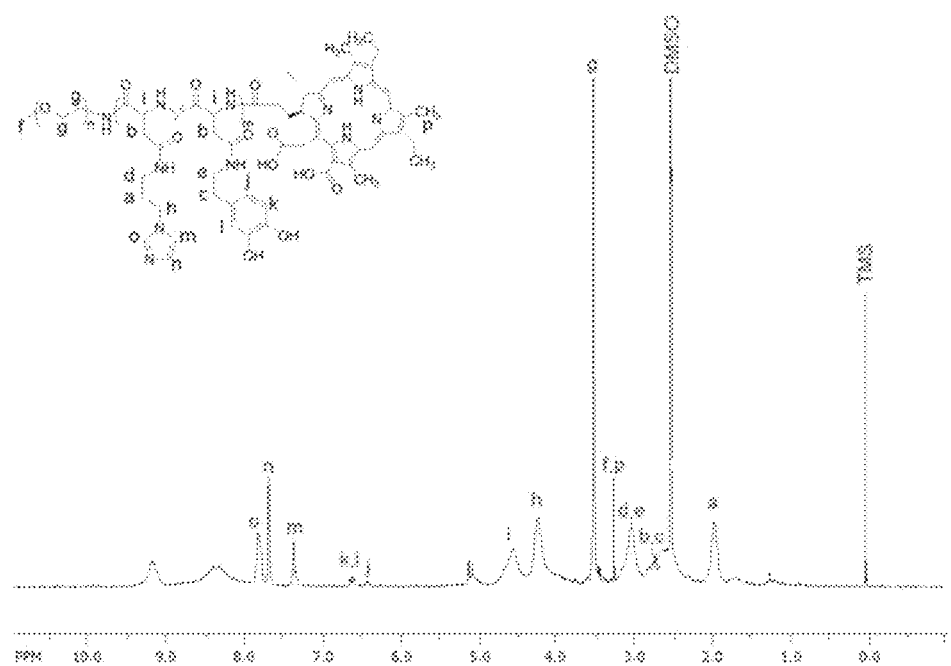
FIG. 2 shows H-NMR analysis of the ligand A (PEG-p(API & DOPA-L-Asp)-Ce6) synthesized in Example 1 of the present invention.

Ligand A was synthesized via aminolysis of the platform ligand with 1-(3-aminopropyl)imidazole (API) and dopamine PEG-PBLA-Ce6 (0.5 g, 18.5 μmol) was dissolved in DMSO (5 mL), followed by the reaction with dopamine (0.1 g, 0.7 mmol) under nitrogen atmosphere at 25° C. for 1 h. Then, API (0.5 g, 3.9 mmol) was added under nitrogen at 25° C. and stirred for 4 h. The reaction mixture was added dropwise into a cooled aqueous solution of 0.1 N HCl (20 mL) and dialyzed against a 0.01 N HCl solution three times (Spectra/Por; MWCO: 1,000 Da). The final solution was lyophilized to obtain ligand A. The H-NMR analysis of ligand A (PEG-p(API & DOPA-L-Asp)-Ce6) at 300 MHz with DMSO-$d_6$ is illustrated in FIG. 2, where δ=7.8 ppm (1H, s, —NCH=N— of imidazole ring), 7.7 ppm (1H, s, —NCH=CH— of imidazole ring), 7.3 ppm (1H, s, —CHC H=N— of imidazole ring), 6.6-6.5 ppm (1H, m, —$CH_2$=C HCH— and —$CH_2CH$=CH— of dopa), 6.4 ppm (1H, m, =CHCO— of dopa), 4.5 ppm (1H, m, —NHCHC=O—), 4.2 ppm (2H, m, =NC$H_2CH_2$), 3.5 ppm (182H, s, —$CH_2C H_2O$— of mPEG chain), 3.0 ppm (2H, m, —NHC $H_2CH_2$—), and 2.8-2.5 ppm (2H, m, CHC$H_2$C=O).

Figure 3:
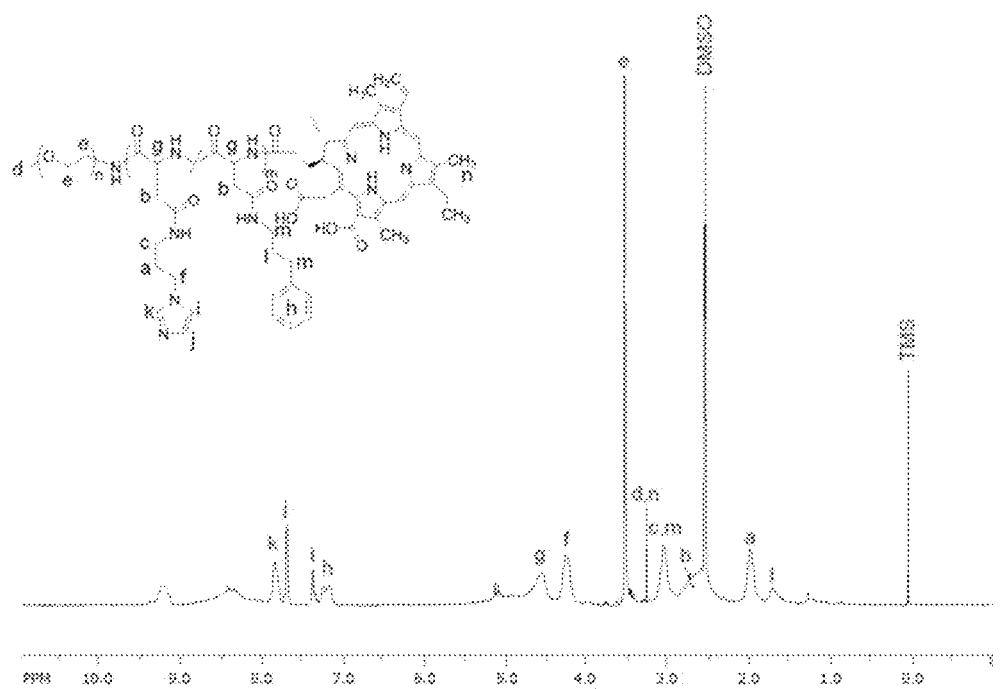
FIG. 3 shows H-NMR analysis of the ligand B (PEG-p(API & PPA-L-Asp)-Ce6) synthesized in Example 1 of the present invention.

Ligand B was synthesized via aminolysis of the platform ligand with API and 3-phenyl-1-propylamine (PPA). PEG-PBLA-Ce6 (0.5 g, 18.5 μmol) was dissolved in DMSO (5 mL), followed by reacting with PPA (0.1 g, 0.9 mmol) under nitrogen at 25° C. for 1 h. Then, API (0.5 g, 3.9 mmol) was added under nitrogen at 25° C. and stirred for 4 h. After the reaction, the mixture was added dropwise into a cooled 0.1 N HCl solution (20 mL) and dialyzed against an aqueous solution of 0.01 N HCl three times (MWCO: 1,000 Da). The final solution was lyophilized to obtain ligand B. The H-NMR analysis of ligand B (PEG-p(API & PPA-L-Asp)-Ce6) 300 MHz with DMSO-$d_6$ is illustrated in FIG. 3, where δ=7.8 ppm (1H, s, —NCH=N— of imidazole ring), 7.7 ppm (1H, s, —NCH=CH— of imidazole ring), 7.3 ppm (1H, s, —CHCH=N— of imidazole ring), 7.3-7.2 (5H, m, —$CH_2C_6H_5$— of PPA), 4.5 ppm (1H, m, —NHC HC=O—), 4.2 ppm (2H, m, =NC$H_2$CH2), 3.5 ppm (182H, s, —$CH_2CH_2O$— of mPEG chain), 3.0 ppm (2H, m, —NHC $H_2CH_2$—), and δ 2.8-2.5 ppm (2H, m, CHC$H_2$C=O.

Figure 4:
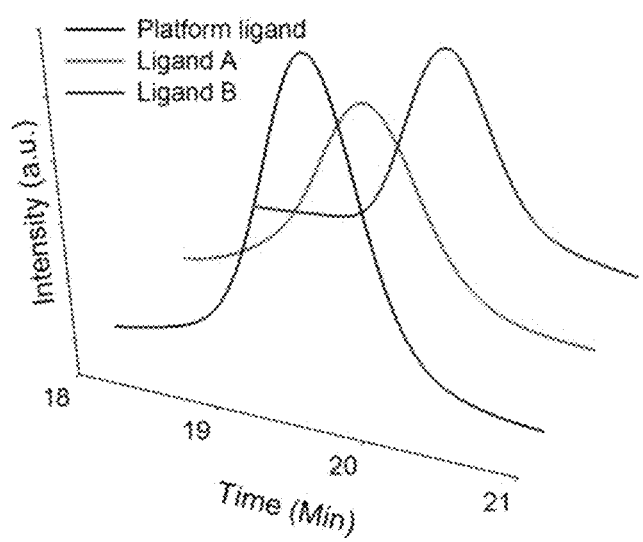
FIG. 4 shows GPC curves of the platform ligand, ligand A and ligand B synthesized in Example 1 of the present invention.

In the GPC measurements (FIG. 4), all polymeric ligands showed unimodal molecular weight distribution indicating no homopolymer residues in the copolymer products. The Ce6 content of the ligand was confirmed by the fluorescence spectroscopy ($\lambda_{ex}$=650 nm and $\lambda_{em}$=675 nm, Table 1).

TABLE 1

Structural characteristics of platform ligand, ligand A and ligand B.

| Code | Copolymer | DP (BLA)[a] | DS (API)[b] | DS (PPA)[c] | DS (Dopa)[d] | DS (Ce6)[e] | PDI[f] | $M_n$[g] |
|---|---|---|---|---|---|---|---|---|
| Platform Ligand | $PEG_1$-$PBLA_{60}$-$Ce6_1$ | 60 | — | — | — | 1 | 1.11 | 16.000 |
| Ligand A | $PEG_1$-$p(API_{55}$ & $Dopa_5$-L-$Asp)_{60}$-$Ce6_1$ | 60 | 55 | — | 5 | 1 | 1.14 | 17.200 |
| Ligand B | $PEG_1$-$p(API_{50}$ & $PPA_{10}$-L-$Asp)_{60}$-$Ce6_1$ | 60 | 50 | 10 | — | 1 | 1.09 | 16.100 |

[a]Degree of polymerization of BLA on the basis of the $^1$H-NMR results.
[b]Degree of substitution of API on the basis of the $^1$H-NMR results.
[c]Degree of substitution of PPA on the basis of the $^1$H-NMR results.
[d]Degree of substitution of Dopa on the basis of the $^1$H-NMR results.
[e]Degree of substitution of Ce6 on the basis of the fluorescence spectroscopy.
[f]Number-averaged ($M_n$), weight-averaged molecular weight ($M_w$) and polydispersity index. (PDI = $M_w/M_n$) were determined by GPC
[g]As determined by $^1$H-NMR.

Example 2. Synthesis of ESIONs

ESIONs were synthesized via thermal decomposition of iron-oleate complex in the presence of oleyl alcohol using the previously reported method (Kim, B. H.; Lee, N.; Kim, H.; An, K.; Park, Y. I.; Choi, Y.; Shin, K.; Lee, Y.; Kwon, S. G.; Na, H. B.; Park, J. G.; Ahn, T. Y.; Kim, Y. W.; Moon, W. K.; Choi, S. H.; Hyeon, T. J. Am. Chem. Soc. 2011, 133, 12624). Briefly, 1.8 g of iron-oleate complex (2 mmol), 0.57 g of oleic acid (2 mmol), and 1.61 g of oleyl alcohol (6 mmol) were dissolved in 10 g of diphenyl ether at room temperature. The mixture was heated to 250° C. at a constant heating rate of 10° C./min and then kept at this temperature for 30 min under inert atmosphere. As the reaction proceeded, the initial brown transparent solution turned black. After the reaction, the mixture containing nanoparticles was removed from the heater and allowed to cool to room temperature, then 50 mL of acetone was added to precipitate the nanoparticles. The nanoparticles were pelleted by centrifuging at 40,000 rpm for 4 hours, the supernatant decanted and the nanoparticles redispersed in n-hexane or chloroform.

Example 3. Fabrication of PMNs

For self-assembly, a solution prepared by mixing 15 mg of Ligand A and 15 mg of Ligand B in 3 mL of DMSO was added slowly to 5 mL of colloidal ESIONs (0.4 mg Fe/mL) in chloroform. The mixture was incubated on a shaker at room temperature for 30 min. Chloroform was then completely removed by evaporation under vacuum and deionized water was added to the colloidal suspension in DMSO to reach a total volume of 5 mL. The DMSO was completely substituted with deionized water using a dialysis membrane (Spectra/Por; MWCO: 12,000 Da). Excess ligands were removed by centrifugation and washed 3~5 times with spin filter (Millipore, MWCO: 100,000 Da, 10,000×g, for 10 min) The resulting nanoparticles were re-dispersed in water.

Example 4. Fabrication of Self-Assembled Ligands

A mixed solution of 15 mg of Ligand A and 15 mg of Ligand B in 3 mL of DMSO was added slowly to 5 mL of chloroform. The mixture was incubated on a shaker at room temperature for 30 min. Then chloroform was removed completely by evaporation under vacuum. Thereafter, deionized water was added to the colloidal solution in DMSO to reach a total volume of 5 mL. DMSO was completely substituted with deionized water using a dialysis membrane (Spectra/Por; MWCO, 12,000 Da). Excess ligands were removed by centrifugation or washed with spin filter (Millipore, MWCO: 100,000 Da, 10,000×g, for 10 min) 3~5 times. The resulting nanoparticles were re-dispersed in water.

Example 5. Fabrication of pH-Insensitive Nanoparticle Assembles (InS-NPs)

A solution prepared by mixing 30 mg of platform ligand in 3 mL DMSO was added slowly to 5 mL of a colloidal ESIONs (0.4 mg Fe/mL) suspension in chloroform. The mixture was incubated on a shaker at room temperature for 30 min. Then chloroform was removed completely by evaporation under vacuum. After this, deionized water was added to the colloidal solution in DMSO to reach a total volume of 5 mL. DMSO was completely substituted with deionized water using a dialysis membrane (Spectra/Por; MWCO, 12,000 Da). Excess ligands were removed by centrifugation or washed with spin filter (Millipore, MW, 100,000 Da, 10000×g, for 10 min) 3~5 times. The resulting nanoparticles were re-dispersed in water.

Example 6. Characterizations of Materials

TEM measurements were performed on a Jeol EM-2010 microscope operated at 200 kV. The powder X-ray diffraction patterns were obtained with a Rigaku D/Max-3C diffractometer equipped with a rotating anode and a Cu Kα radiation source ($\lambda$=0.15418 nm). The present inventors performed elemental analysis by inductively coupled plasma atomic emission spectroscopy (ICP-AES) using an ICPS-7500 spectrometer (Shimadzu) and inductively coupled plasma—optical emission spectrometer (ICP-OES) (Perkin-Elmer Optima 4300 DV). UV/visible absorption spectra were collected on UV-2450 spectrophotometer (Shimadzu, Japan). Particle size and zeta potential were measured with a Zetasizer Nano ZS (Malvern Instruments, Malvern, UK). For the size data analysis, material refractive index (2.42), material absorbance (0.2), dispersant refractive index (1.33), and dispersant viscosity (0.8872) were used. The magnetic properties were investigated using a superconducting quantum interface device (SQUID) magnetometer (Quantum Design MPMS XL). Hydrodynamic sizes were obtained using dynamic light scattering (DLS) (Zetasizer Nano ZS (Malvern Instruments, Malvern, UK)) instrument at 25° C.

Example 7. Measurements of Critical Aggregation Concentration (CAC)

A stock solution of Hoechst 33342 ($1.4 \times 10^{-3}$ M) in double-distilled water was prepared and stored at 4° C. The Hoechst 33342 solution was mixed with solutions containing the samples at the concentrations of $1.0 \times 10^3$ mg/mL to 1.0 mg/mL. The final concentration of Hoechst 33342 in each sample solution was $7.0 \times 10^{-4}$ M. The resultant fluorescence was measured on a RF-5301PC (Shimadzu, Japan) with $\lambda_{ex}$=355 nm and $\lambda_{em}$=457 nm and the slit widths were ex=3 nm and em=3 nm, respectively.

Example 8. Transmittance Measurement of PMNs at Different pH

The light transmittance measurements of PMN solutions (2 mg/mL, without Ce6 attachment) were obtained using a UV-Visible spectrophotometer at 500 nm while the pH value of solution was gradually decreased from 7.5 to 4.0 by adding 0.1 N HCl, and increased from 4.0 to 7.5 by adding 0.1 N NaOH solution.

Example 9. pH-Dependent Fluorescence Intensity Measurement

The fluorescence intensity of PMNs or self-assembled ligands (2 mg/mL, 650 nm excitation and 675 nm emission) was measured using a fluorescence plate reader (Tecan Genios, Durham, N.C.), while the pH of the solution was gradually decreased from 7.5 to 4.0 by adding 0.1 N HCl solution.

Example 10. pH-Dependent Singlet Oxygen Generation (SOG) Measurement

To evaluate the SOG, samples (2 mg/mL, 100 μL) at different pH were mixed with singlet oxygen sensor green (SOSG, 2.0 μM, 100 μL). SOG was induced by irradiation with a 670-nm laser source (Institute of Electronics) at 5 mW/cm$^2$ intensity for 4 min. SOSG fluorescence was detected ($\lambda_{ex}$=494 nm and $\lambda_{em}$=534 nm) after irradiation to determine the SOG of the samples. SOG was evaluated by SOSG fluorescence enhancement compared to the background.

Example 11. Cell Culture

HCT116 (human colon cancer, KCLB No. 10247) cells, CT26 (murine colorectal carcinoma cell, KCLB No. 80009) and M2-10B4 (murine bone marrow stromal cell, KCLB No. 21972) were obtained from the Korean Cell Line Bank. HCT116 cells were cultured in 10 mL of Roswell Park Memorial Institute (RPMI-1640) medium supplemented with 10% fetal bovine serum (FBS) and 1% penicillin/streptomycin. CT26 cells were cultured in Dulbecco's Modified Eagle Medium (DMEM) supplemented with 10% FBS and 1% penicillin/streptomycin. M2-10B4 were cultured in RPMI-1640 medium supplemented with 10% FBS and 1% penicillin/streptomycin. Culturing conditions for all cells were 37° C. in 100% humidity and 5% $CO_2$. Drug resistant CT26 cells (CT26/MDR) were developed by exposing CT26 cells to increasing doses (1, 5, 10, 25, 50, 100, 500, 1,000, and 5,000 ng/mL) of DOX for 24 h followed by 3-4 days of recovery before exposing to the next dose. CT26/MDR were then frozen and stored in liquid nitrogen. Fresh aliquots of CT26/MDR were used in all experiments to ensure that they did not revert to a drug sensitive phenotype.

Example 12. pH-Dependent Cell Uptake

HCT116 cells were exposed to PMNs, InS-NPs and Ce6 at different pHs to verify their cellular uptake respectively. The cells were incubated for 2 h, washed, harvested, and re-suspended with DPBS. In vitro cellular uptake was quantified using a flow cytometer (Beckman, San Jose, Calif., USA). For each sample 10,000 cells (gated events) were counted, and free Ce6 fluorescence was detected with logarithmic settings (FL4; $\lambda_{em}$=670 nm). Cells were counted as positive if their fluorescence (FL4) was higher than that of cells from an untreated cell suspension. Each experiment was analyzed statistically using the CXP Analysis Program.

Example 13. Confocal Laser Scanning Microscope

Confocal laser scanning microscope (LSM 510 Meta; Zeiss, Germany) was used to carry out fluorescence imaging. An optimal pinhole size of 120 μm was selected to exclude fluorescent light emitted from out-of-focus planes above and below the focusing plane. The excitation/emission wavelengths were 340/488 nm for DAPI, 490/520 nm for FITC, 555/578 nm for RITC, and 650/670 nm for Ce6. Fluorescence images were analyzed using LSM Image Browser software (Zeiss).

Example 14. Cell MR Imaging

To label the cells with PMNs, HCT116 cells were seeded onto culture dishes in 10 mL of media and grown overnight. Subsequently, PMNs of 0, 12.5, 25, and 50 μg/mL were added. After 4 h, the cells were washed twice with PBS and detached by adding 1 mL of trypsin/EDTA. After centrifugation, cells were dispersed in culture media and transferred to a 1.5 mL test tube. Cell pellets were prepared by centrifugation at 1,000 rpm for 5 min. $T_1$-weighted MR images were acquired with a head coil on a 1.5 T MR scanner (Signa Excite, GE Healthcare).

Example 15. Pharmacokinetic Analysis

For the plasma concentration-time experiment, the mice were injected with PMNs and InS-NPs respectively (2 mg Fe/kg) via the tail vein. Blood was collected at 1 min, 30 min, 1 h, 3 h, 8 h and 20 h after the injection. Plasma was isolated from red blood cells by centrifugation at 1,000 rpm for 10 min. The plasma (100 μL) for each blood sample was subsequently mixed with 70% nitric acid (1 mL) at room temperature for 12 h followed by centrifugation (10,000 rpm for 5 min), and the supernatant was used for inductively coupled plasma optical emission spectrometer analysis (ICP-OES, Optima 4300 DV, Perkin-Elmer) after 5-fold dilution with 2% nitric acid. Fe uptake in the tumor was measured 12 h after PMNs or InS-NPs injection (2 mg Fe/kg). Dissected tumor tissues were weighed, homogenized, and treated with scintillation mixtures. A volume of 60% nitric acid was added to each sample and tissue was incubated for 24 h at 60° C. after which the solutions were centrifuged at 13,000 rpm for 30 min and the supernatant was diluted 10-fold with 2% nitric acid. Determination of Fe uptake content in tumor was performed by ICP-OES, and the nanoparticle uptake in tumor was calculated as gram of Fe content per gram of tissue (g Fe/g Tissue).

Example 16. Immunohistochemistry

Tumor tissues were fixed in 10% neutral buffered formalin and frozen sectioned into 5 micron thick slices. SDF-1 and P-gp were immunolabeled with anti-SDF-1 antibody (abcam) and anti-P-glycoprotein antibody (abcam), then the samples were incubated for 60 min at ambient temperature with RITC ($\lambda_{ex}/\lambda_{em}$, 555/578 nm) or FITC ($\lambda_{ex}/\lambda_{em}$, 490/520 nm) conjugated secondary antibody for further confocal laser scanning microscope analysis.

Example 17. Tumor Histology

For histology analysis, tumor tissues from control and treated mice were fixed in 10% neutral buffered formalin and frozen sectioned into 5 micron thick slices, stained with hematoxylin & eosin (H&E) and terminal deoxynucleotidyl transferase dUTP nick-end labeling (TUNEL), and were examined by a digital microscope (Leica QWin) and a confocal laser scanning microscope (LSM 510 Meta; Zeiss, Germany).

Example 18. In Vivo Toxicity Evaluation of PMNs

Healthy nude mice were intravenously injected with a suspension of PMNs or normal saline (control group). After 2 weeks, the mice were sacrificed and major viscera collected. The heart, liver, spleen, kidney, and lung were stained with H&E. Reagent kits of ALT, AST, ALP and D-LDH were employed to analyze the serum which was isolated from blood sampled by eyeball extirpation.

Example 19. In Vitro Cellular Uptake

The tumor cellular uptake of PMNs was monitored at different pH conditions (pH 7.4 and 6.8) using a KODAK In vivo Image Station (Image Station 4000 MM; Kodak, New Haven, Conn., USA) and a flow cytometer (Beckman, San Jose, Calif., USA). HCT116 cells ($1\times10^5$ cells/mL) were incubated with each sample for 2 h in RPMI-1640 medium (pH 7.4 or 6.8, with 1% penicillin-streptomycin) at 37° C. and then analyzed. To ameliorate photobleaching during microscope observation, a drop of anti-fade mounting solution (5% N-propyl gallate, 47.5% glycerol, and 47.5% Tris-HCl, pH 8.4) was added to the cells.

Example 20. In Vivo Studies

All in vivo studies conformed to the Guide for the Care and Use of Laboratory Animals published by the National Institutes of Health, USA (NIH publication no. 85-23, 1985, revised 1996), and mice were maintained under the guidelines of an approved protocol from the Institutional Animal Care and Use Committee (IACUC) of the Catholic University of Korea (Republic of Korea).

Example 21. Characterization of PMNs

Figure 14:
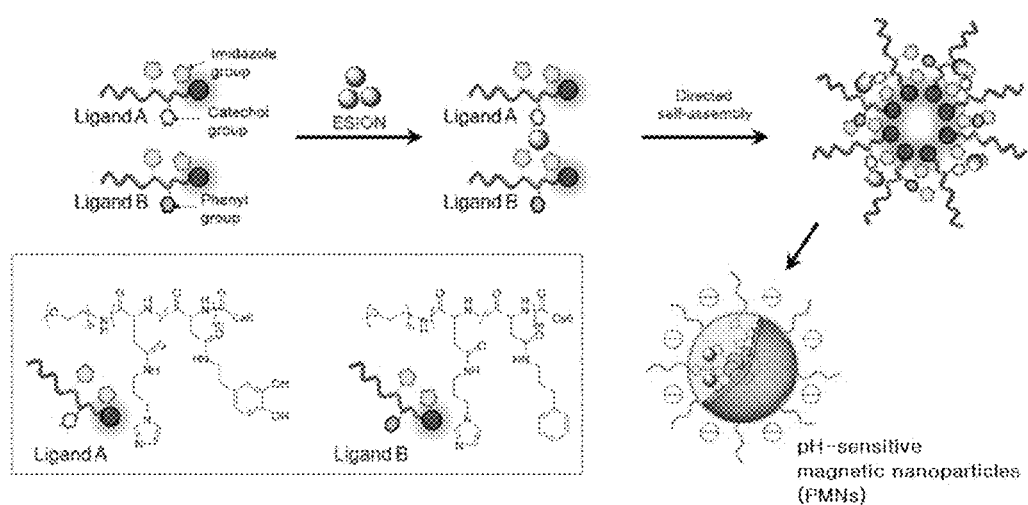
FIG. 14 shows the PMNs that were fabricated by coassembly of ESIONs, ligand A and ligand B.

Ce6 grafted poly(ethylene glycol)-poly(β-benzyl-L-aspartate)(PEG-PBLA-Ce6) was synthesized to provide a platform ligand in which the flanking benzyl ester groups readily react with primary amines via nucleophilic attack. Imidazole (pKa, ~6.8) was then easily incorporated as an ionizable group to impart pH sensitivity to the tumor microenvironment. On the basis of this platform, the present inventors further engineered two ligand derivatives: ligands A and B. For ligand A, catechol groups were added to facilitate self-assembly as they can act as high-affinity anchors for iron oxide nanoparticles. In contrast, the hydrophobicity of ligand B was tuned using 3-phenyl-1-propylamine to produce a critical phase transition of PMNs that is activatable by tumor endo/lysosomal pH of ~5.5. The PMNs were fabricated by coassembly of ESIONs, ligand A and ligand B (Scheme 2) (FIG. 14).

Figure 15:
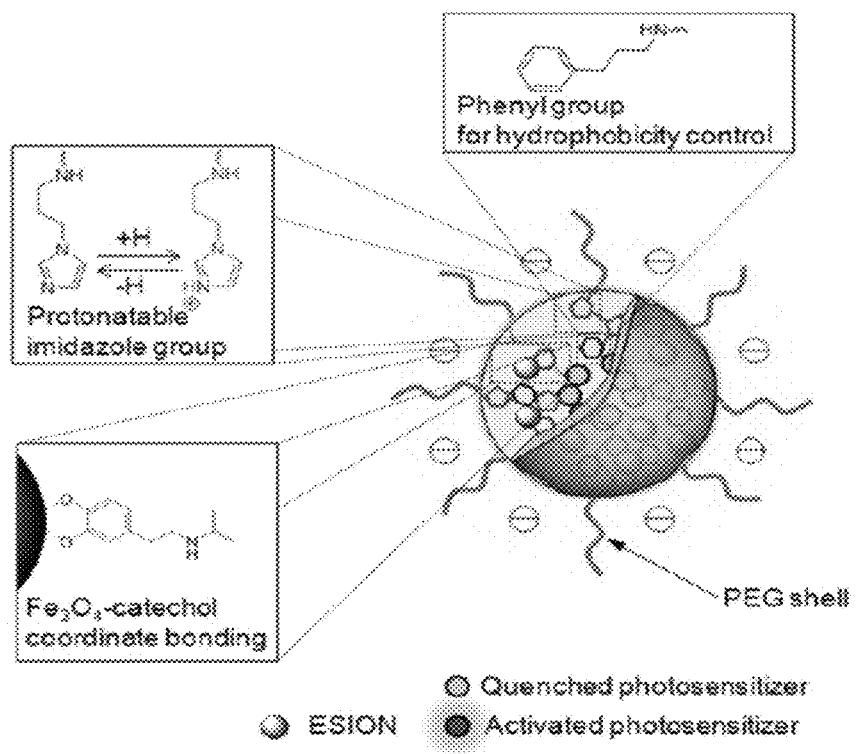
FIG. 15 shows selfassembly of ESIONs into colloidal magneto-core shell structures.
Figure 16:
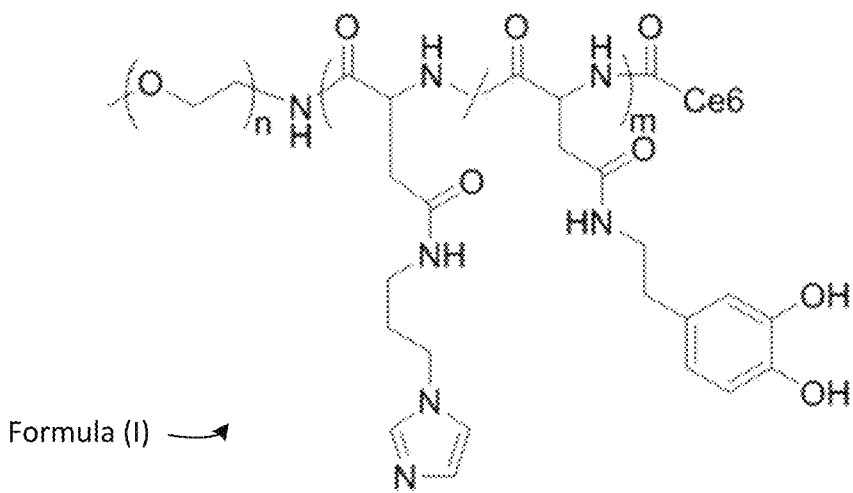
FIG. 16 shows an embodiment of ligand A.
Figure 17:
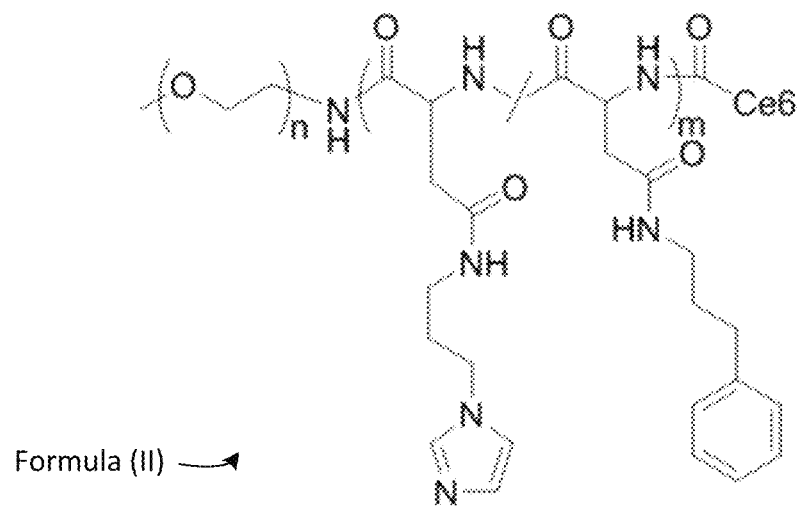
FIG. 17 shows an embodiment of ligand B.

Because ESIONs (~3 nm) were much smaller than the hydrodynamic dimensions of the peptide block of the ligands (~60 residues; length of ~20 nm), the catechol-anchored ligand A could wrap around the periphery of the ESIONs. These functionalized ESIONs can thus be considered polymer-metal analogues of conventional amphiphilic diblock copolymers since the functionalization permitted directed selfassembly of ESIONs into colloidal magneto-core shell structures (Scheme 3) (FIG. 15). The hydrophobic core is then composed of the ESIONs and hydrophobic blocks of the tumor-sensing polymeric ligands.

Figure 5A:
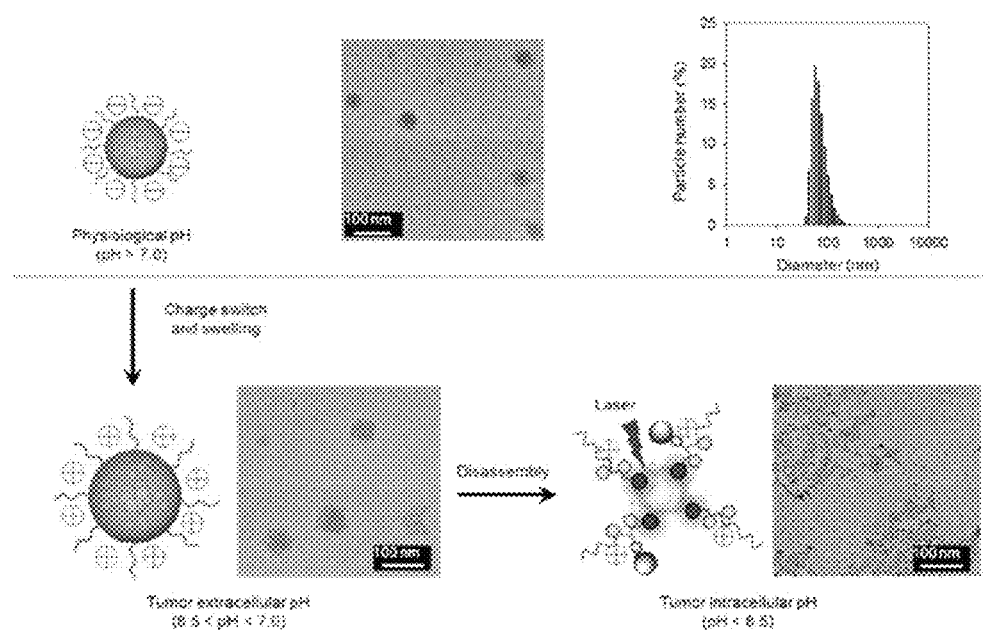
FIG. 5a shows pH-dependent structural transformation change in pH-sensitive magnetic nanoformulation (PMN): self-assembly of iron oxide nanoparticles and pH-responsive ligands (inset of (a): TEM images of PMNs at pH 7.4, 6.8, and pH 5.5, DLS measurement of PMN colloidal dispersion at pH 7.4 showing an average diameter of ~70 nm).
Figure 6A:
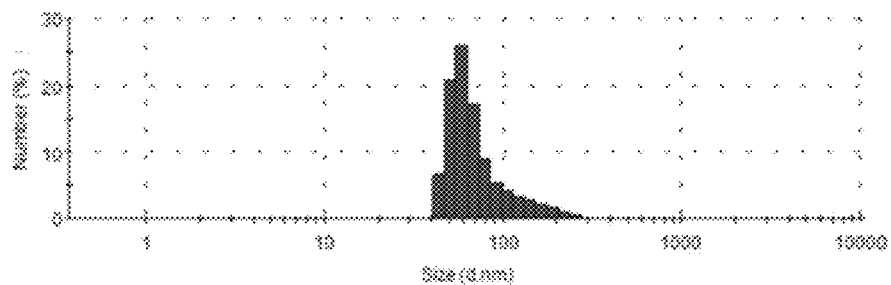
FIG. 6a shows size distribution by number.
Figure 6B:
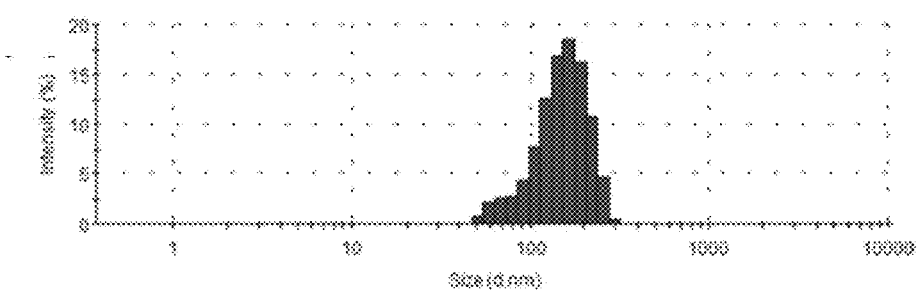
FIG. 6b shows size distribution by intensity.
Figure 6C:
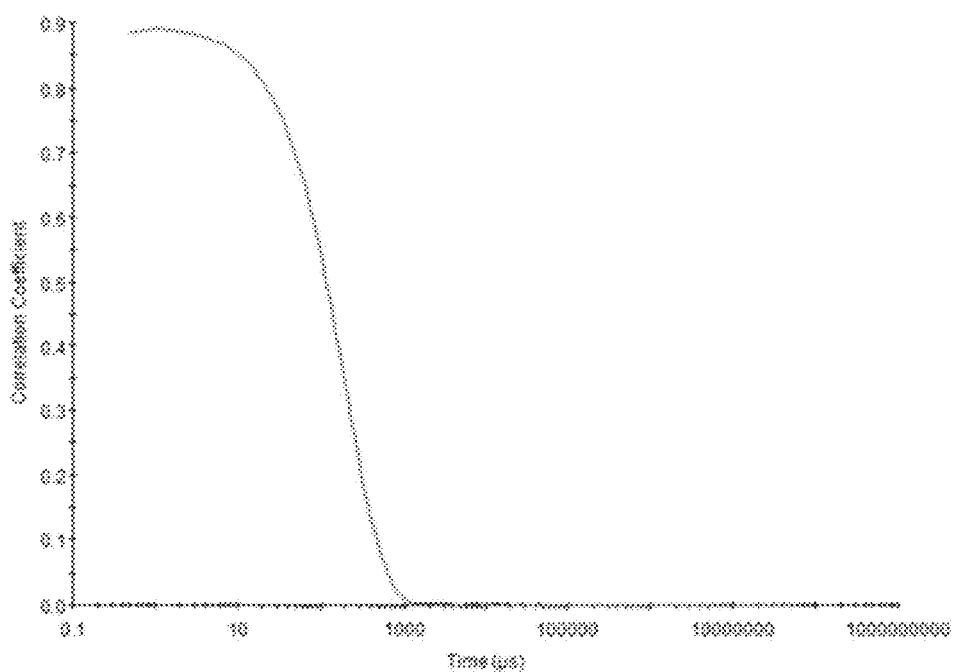
FIG. 6c shows raw correlation data of InS-NP colloidal dispersion at pH 7.4.

Transmission electron microscopy (TEM) (FIG. 5a) revealed the particle size of PMNs is ~60 nm. They were well dispersed in water, and the hydrodynamic diameter measured by dynamic light scattering (DLS) was found to be 70±5 nm (FIG. 5a), which is appropriate for the enhanced permeability and retention (EPR) effect for passive tumor targeting. As a control, the present inventors fabricated pH-insensitive nanoparticle assemblies (denoted as InS-NPs) by assembling ESIONs and the platform ligand, which were similarly sized to PMNs (FIG. 6).

Figure 5B:
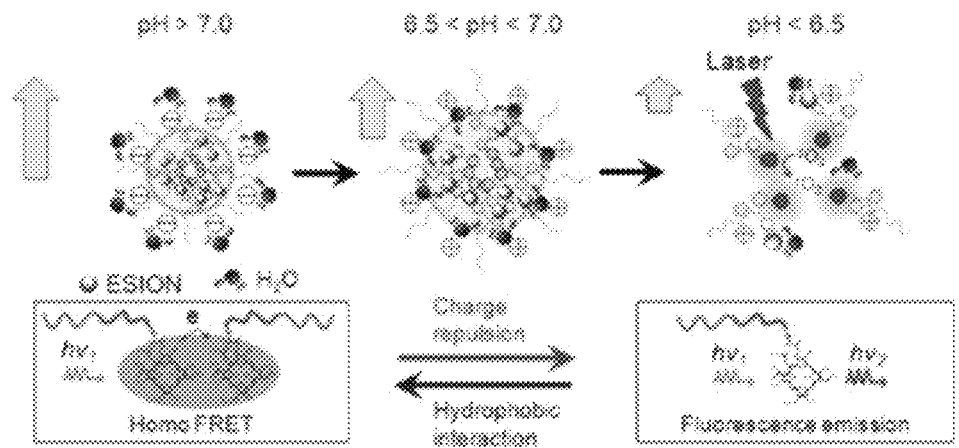
FIG. 5b shows schematic representation of pH-dependent structural transformation and related magnetic/photoactivity change in PMNs.
Figure 5C:
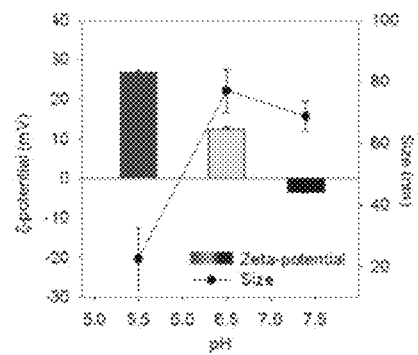
FIG. 5c shows zeta-potential and DLS size measurement of PMNs (0.1 mg/mL) as a function of pH following a 1 h incubation (n=3) (DLS measurements were conducted using a material refractive index of 2.42, solvent refractive index of 1.33 (water) and a viscosity of 0.8872).
Figure 7A:
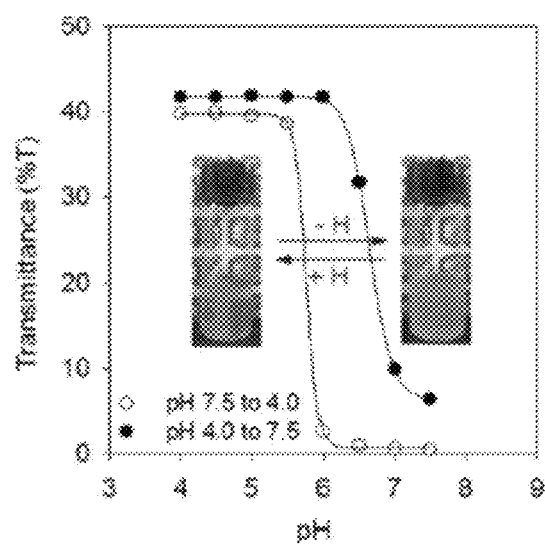
FIG. 7a shows transmittance of PMN suspension measured at selected pH values (the inset photo presents data for pH-dependent turbidity of the PMN solution with a transition pH value of ~6.0. The pH was gradually changed from 4.0 to 7.5 (●) and from pH 7.5 to 4.0 (○)).
Figure 7B:
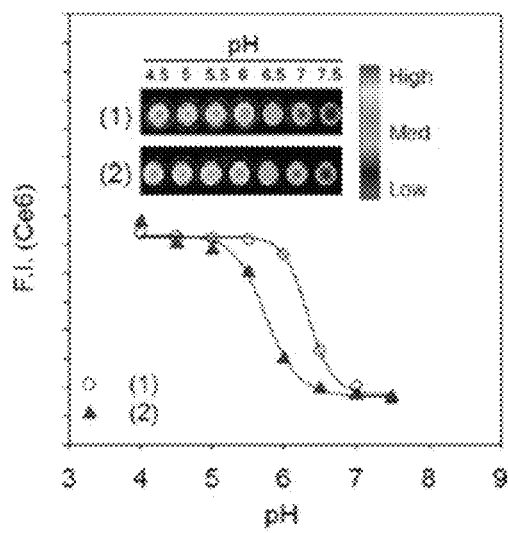
FIG. 7b shows pH-dependent fluorescence intensity and near-infrared fluorescence imaging of (1) self-assembled ligands and (2) PMNs.
Figure 7C:
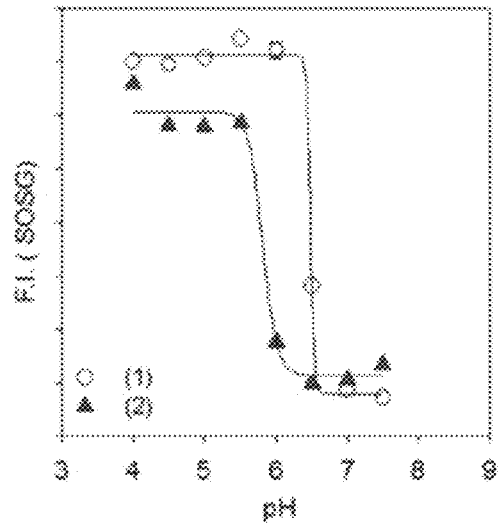
FIG. 7c shows pH-dependent singlet oxygen generation of (1) self-assembled ligands and (2) PMNs.

New ligand design of the present invention enabled a two-stage pH activation leading to surface charge reversal in the tumor periphery for increased cell adsorption and permeation as well as endo/lysosomal pH dependent theranostic activity of PMNs. This pH-dependent structural transformation is schematically presented in FIG. 5b. First, PMNs are slightly negatively charged at pH 7.4. The drop in pH within the tumor environment causes increased imidazole ionization which reverses the polarity of the complex causing it to swell (FIG. 5c), thereby enhancing their payload delivery and cell internalization due to electrostatic interactions with the vicinal anionic cells. Upon internalization, the particles further ionize as the endosomal pH decreases to 5.5-6.0. Here the hydrophobic interactions of the core of the PMNs weaken, and the ionized unimers repel each other leading to complete dissociation as confirmed by both DLS (FIG. 5c) and TEM (FIG. 5a). Acid-base titration (FIG. 7a) demonstrated a sharp drop in transmittance (% T) at the critical pH range of 5.5-6.0. When the pH was increased again, % T recovery was hysteretic, thereby demonstrating a reversible pH-dependent assembly/disassembly process. Consequently, the photoactivity, i.e. singlet oxygen generation (SOG) and fluorescence, of PMNs was quenched at pH 7.4 due to fluorescence resonance energy transfer. At pH<6, the photoactivity was dramatically recovered upon disassembly, similar to that observed for the other self-assembled polymeric ligands (FIGS. 7b and 7c). Interestingly, PMNs showed a 2-fold lower critical aggregation concentration (~0.01 mg/mL) than the self-assembled polymeric ligands possibly due to polymer chain entanglement indicating their improved colloidal stability.

Figure 7D:
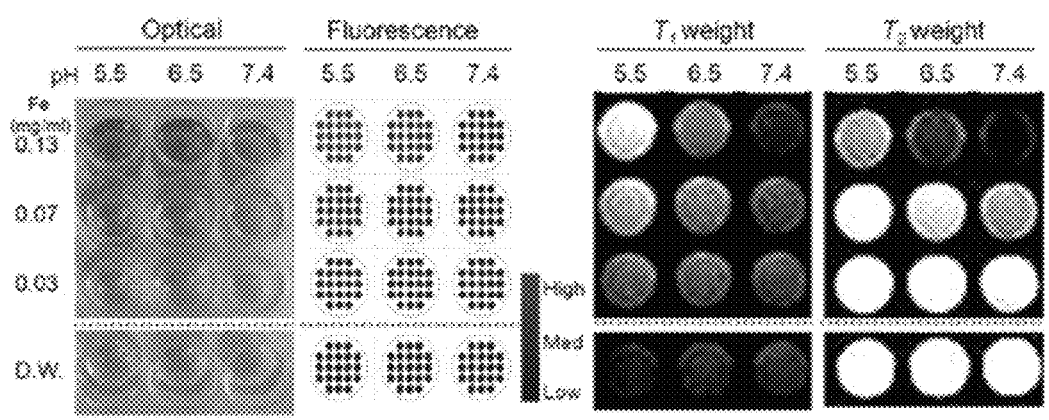
FIG. 7d shows optical, fluorescence, and MR phantom images (examined in a clinical 1.5 T MRI scanner) of a concentration gradient of PMNs at three different pH values.
Figure 7E:
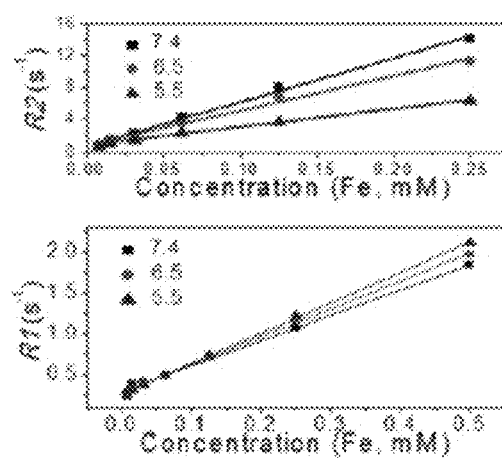
FIG. 7e shows pH-dependent magnetic relaxation properties of PMNs.
Figure 8:
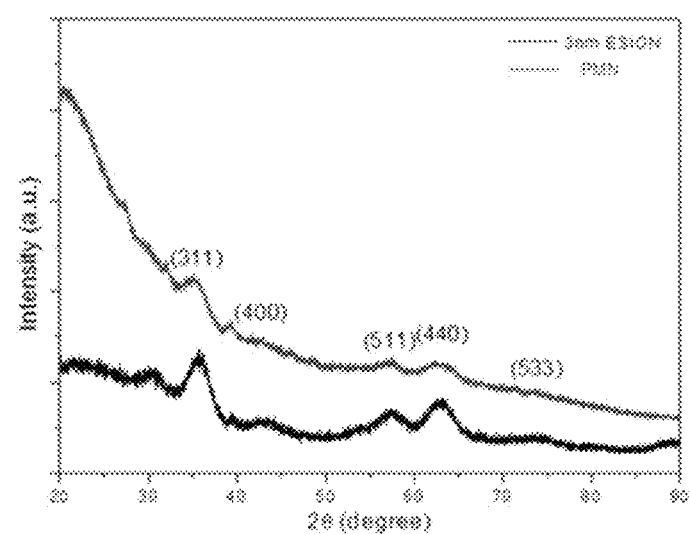
FIG. 8 shows the XRD patterns of PMNs and 3 nm-sized ESIONs (extremely small iron oxide nanoparticles).
Figure 9A:
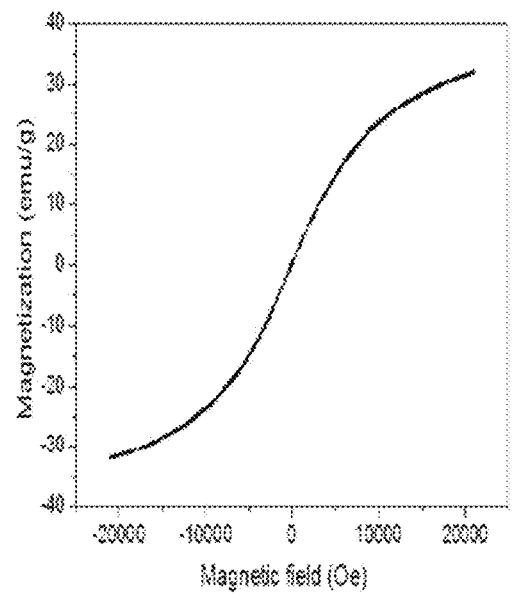
FIG. 9a shows M-H curve between the magnetic field of 20 kOe and −20 kOe.
Figure 9B:
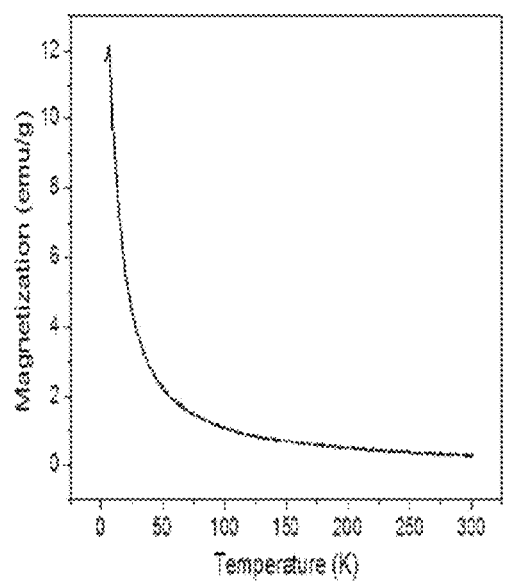
FIG. 9b shows M-T curve under 100 Oe with the temperature varying from 300 to 4 K of PMN.
Figure 10:
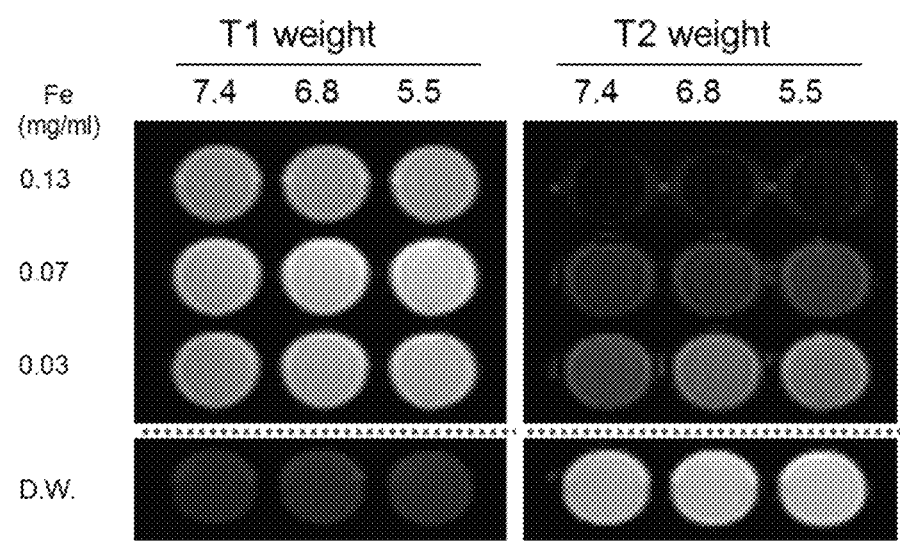
FIG. 10 shows MR phantom images of a concentration gradient of InS-NPs at three different pH values.

The X-ray diffraction (XRD) pattern of PMNs was similar to that of ESIONs (FIG. 8), and the PMNs show a weak magnetization because of the spin-canting effect (FIG. 9). The pH-dependent structural transformation of PMNs in water is expected to affect proton relaxation. Considering the large number of high-spin Fe(III) ions with five unpaired electrons (S=5/2) on the surface of ESIONs, direct water coordination with $Fe^{3+}$ species is a major contributor to the longitudinal relaxivity (r1) of PMNs. The intensity variation of the $T_1$ MR phantom of PMNs at different pH values (same Fe concentration) was well matched with the corresponding fluorescent imaging results (FIG. 7d). PMNs showed an r1 of 3.30 $mM^{-1} \cdot s^{-1}$ with a transverse relaxivity (r2) of 43.95 $mM^{-1} \cdot s^{-1}$ at pH 7.4, and a concomitant r1-increase and r2-decrease was observed as the pH decreased from 7.4 to 5.5 (FIG. 7e). It is assumed as pH decreases, ligands become protonated and gain hydrophilicity. Consequently, both the number of coordinated water molecules and the duration of their coordination with $Fe^{3+}$ will increase. Moreover, as pH-induced disassembly occurs, separated ESIONs exhibit a lower r2 compared to initial PMNs. Although the efficiency of the contrast effect is evaluated in terms of relaxivity (r1), the r2/r1 ratio also plays an important role in positive $T_1$ imaging as an excessively high r2 may preclude their use as $T_1$ contrast agents. As the pH decreases, the r2/r1 ratio of PMNs significantly decreases along with r2. Finally, the PMNs have a specific r1 value of 3.87 $mM^{-1} \cdot s^{-1}$ and a low r2/r1 ratio of 5.8 at pH 5.5, which results in a bright signal in $T_1$-weighted imaging. Therefore, the positive $T_1$ MR contrast of PMNs was quenched at pH 7.4 but greatly recovered at pH 5.5, which indicates PMNs can be used for sensitive $T_1$ MR imaging of acidic tumor regions. In contrast, MR contrast of InS-NPs was not dependent on pH (FIG. 10). To the best of the present inventors knowledge, this is the first demonstration of biocompatible iron oxide nanoparticles showing pH-sensitive $T_1$ contrast that can be used for tumor pH-sensitive $T_1$ MR imaging. Although $Gd^{3+}$-based $T_1$ contrast agent can also be designed to respond to pH stimulus, they generally have short blood half-lives, preventing their accumulation in tumors for high-resolution tumor imaging. Furthermore, $Gd^{3+}$-based contrast agents can be potentially toxic; severe side effects were observed in patients with renal failure that received gadolinium-containing contrast agents, such that the U.S. FDA recently released a warning regarding $Gd^{3+}$-based MR contrast agents and nephrogenic system fibrosis (NSF). While such side effects are quite rare, occurring in less than 5% of patients, the present inventors believe iron oxide nanoparticles may provide a more biologically and metabolically compatible alternative. The use of biodegradable polymeric peptides for iron oxide-based PMN fabrication gives the final product a longer blood half-life and a greater biocompatibility for clinical translation.

Example 22. In Vitro and In Vivo MRI

MRI investigations were conducted using a 1.5 T MR scanner (Signa Excite; GE Healthcare) by using a Litz Coil (diameter, 100 mm; length, 85 mm; DOTY Scientific Inc., NC, USA). Spin-lattice and spin-spin relaxation times ($T_1$ and $T_2$) were measured using fast spin echo (FSE) sequence for different concentrations of PMNs in media with different pH values at room temperature. For $T_1$ measurements, the Field of View (FOV) was set to 75×75 mm, slice thickness (SL)=3 mm, Echo time (TE)=9.3 ms and Repetition Time (TR)=505.2, 525.0, 545.0, 565.0, 585.0, 605.0, 625.0, 645.0, 665.0, 685.0, 705.0, 730.0, 755.0, 805.0, 855.0, 905.0, 955.0, 1005.0, 1055.0, 1105.0 ms. For $T_2$ measurements, the following parameters were used: FOV=100 mm*100 mm, SL=3 mm, TR=4,000 ms, TE=10.9, 21.7, 43.5, 54.4, 65.2, 87.0, 119.6, 141.3, 163.1, 174.0 ms. The longitudinal (r1) and transverse (r2) relaxivities were calculated from $r_i=(1/T_i-1/T_{i0})/c$, where c is the Fe concentration of PMNs in mM, $T_i$ is the relaxation time at concentration c, $T_{i0}$ is the relaxation time of water, and i=1 and 2 for $T_1$ and $T_2$. The cellular MR images were acquired using FSE sequence (FOV=100 mm*100 mm, SL=3 mm) For $T_1$ measurement, TR=400 ms and TE=10 ms were used, whereas for $T_2$ measurement, TR=4,000 ms and TE=86.72 ms were used. For the MR diagnosis of tumor in vivo, PMNs were injected through the tail vein at a dose of 2 mg Fe/kg body weight. Mice were then placed in a 1.5 T MR scanner (Signa Excite, GE Healthcare), and FSE sequence was used with the followed parameters: FOV=90 mm×90 mm, SL=2 mm, Flip angle (FA)=90°, for $T_1$ MR imaging, TR=400 ms, TE=10 ms, and for $T_2$ MR imaging, TR=3,000 ms, TE=101 ms. The transverse section images were obtained and analyzed using Onis Dicom Viewer (DigitalCore, Tokyo, Japan).

Figure 11A:
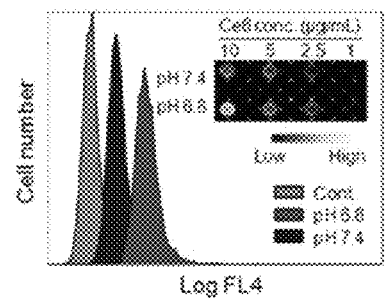
FIG. 11a shows cellular uptake of PMNs (equivalent to 1 μg/mL Ce6) for HCT116 cancer cells at pH 7.4 or 6.8 (4 h incubation) analyzed using flow cytometry (the inset shows near-infrared fluorescence imaging of HCT116 cancer cells treated with different concentrations of PMNs at pH 7.4 and 6.8 (4 h incubation)).
Figure 11B:
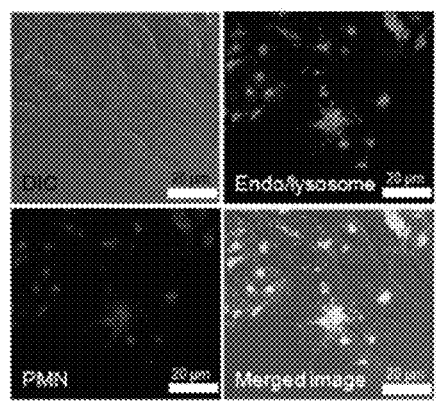
FIG. 11b shows confocal microscopy images of activated PMNs in HCT116 cancer cells (the endosomes/lysosomes were stained with Lysotracker Green which selectively labels lysosomes).
Figure 11C:
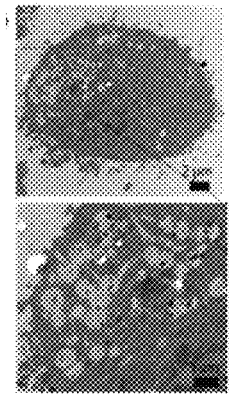
FIG. 11c shows BioTEM images of PMN uptake by HCT116 cancer cells.
Figure 11D:
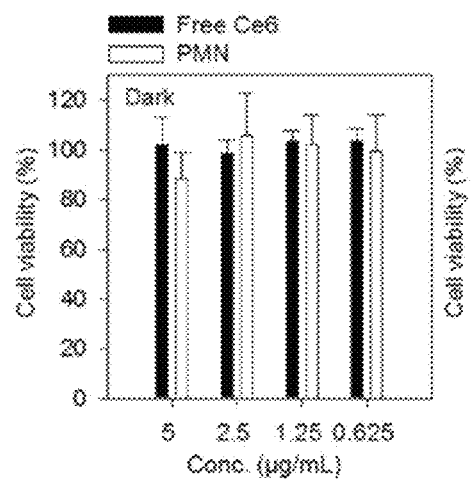
FIG. 11d shows MTT assays of HCT116 cells exposed to PMNs and free Ce6 without laser irradiation.
Figure 11E:
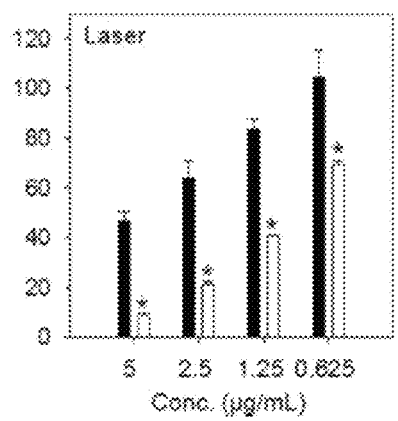
FIG. 11e shows MTT assays of HCT116 cells exposed to PMNs and free Ce6 with laser irradiation.
Figure 11F:
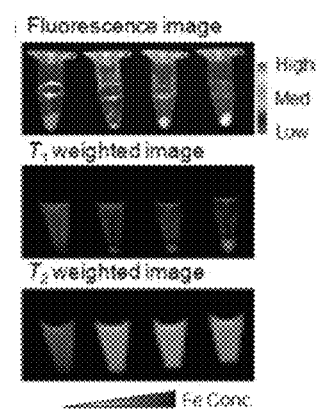
FIG. 11f shows fluorescence (upper) and MR (lower) images of HCT116 cancer cell pellets (1×10⁶ cells) incubated with various concentrations of PMNs (0, 12.5, 25, or 50 μg Fe/mL) for 4 h.

PMNs showed higher cellular uptake at pH 6.8 than at pH 7.4 as evidenced by both fluorescence and flow cytometry results (FIG. 11a). In contrast, the cellular uptake of Ce6 and InS-NPs was not affected by changes in pH. For cell uptake, the present inventors followed the iron oxide nanoparticles by TEM (FIG. 11c) which shows uptake in endosomes. The present inventors also followed the Ce6 dye by confocal laser scanning microscopy (CLSM) (FIG. 11b) which shows the fluorescence of PMNs merges perfectly with that of Lysotracker Green. The existence of the Ce6 signal suggests PMNs indeed disassembled for fluorescence dequenching here in the endosome. Consequently, PMNs showed no cytotoxicity in the dark (FIG. 11d) but induced cell death much more efficiently than Ce6 under illumination (FIG. 11e) at pH 6.8. MR contrast and fluorescence of human colorectal carcinoma (HCT116) cells labeled with PMNs (FIG. 11f) further confirmed their dual-modal imaging capability.

Figure 12F:
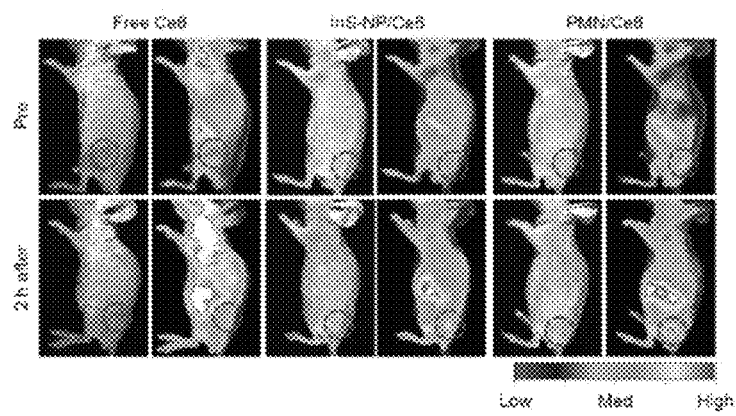
FIG. 12f shows in vivo NIR imaging of nude mice bearing HCT116 tumors after intravenous injection of PMNs, InS-NPs or free Ce6 (equivalent to 0.2 mg/kg Ce6).
Figure 12G:
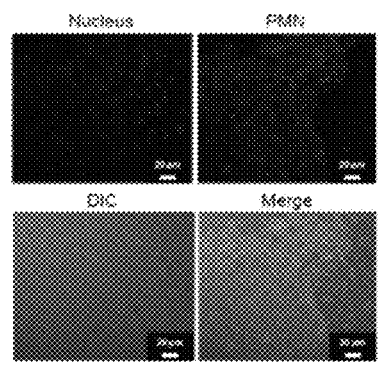
FIG. 12g shows CLSM shows Ce6 uptake by tumor cells in tumor tissue of nude mice after intravenous injection of PMNs (the dashed regions in (a, b, f) indicate tumor sites).
Figure 13A:
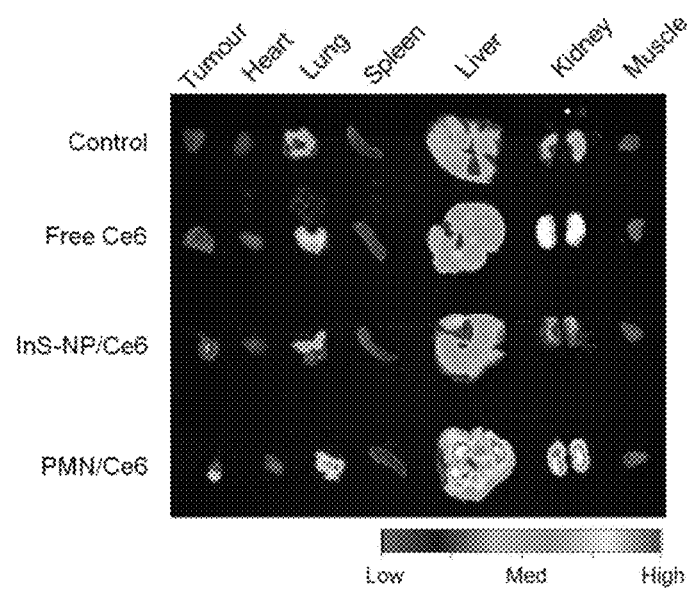
FIG. 13s shows fluorescent images of organs extracted 24 h post-treatment.
FIG. 13b shows measured signal intensities of organs extracted 24 h post-treatment.
Figure 13B:
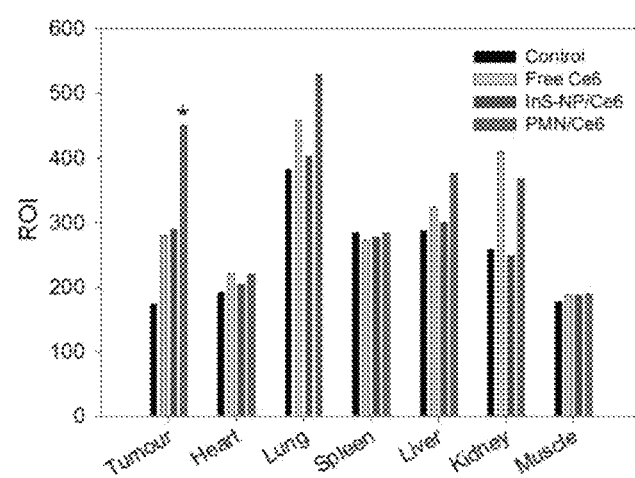

The present inventors performed in vivo early stage tumor diagnosis with PMNs. Without conjugation of any tumor-targeting moiety and in contrast to InS-NP injection, PMN injection resulted in significant $T_1$ enhancement of ultrasmall HCT116 tumors of ~3 mm in diameter (FIGS. 12a-12c), thus confirming their successful tumor targeting and pH-dependent $T_1$ MR contrast effect. pharmacokinetic studies showed both PMNs ($t_{1/2,PMN}$=2.90 h) and InS-NPs ($t_{1/2,InS-NP}$=2.19 h) had long blood circulation times (FIG. 12d). However, notably, PMN accumulation in tumors was >2-fold higher than that of InS-NPs (FIG. 12e). Moreover, PMNs also enabled high-resolution fluorescent imaging of tumors in mice (FIG. 12f). Macroscopic fluorescent imaging of excised organs demonstrated significant tumor accumulation of PMNs (FIG. 13), and subcellular CLSM confirmed uptake of PMNs by tumor cells (FIG. 12g). These results indicate PMNs are promising candidates for highly efficient early diagnosis of cancer.

What is claimed is:

1. A ligand composition for use with a MRI contrasting agent comprising:
a ligand A having the following structure:

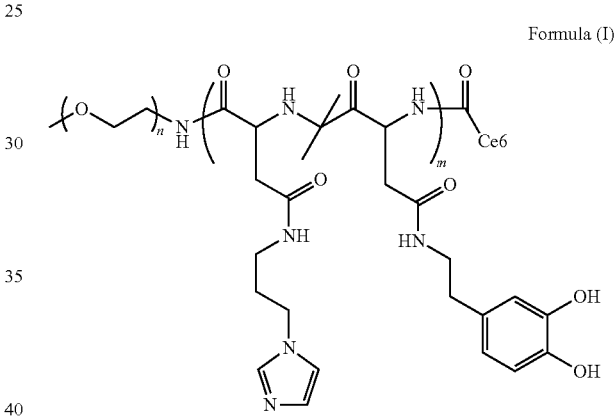

Formula (I)

wherein n and m are independently an integer of 5-500,
a ligand B having the following structure:

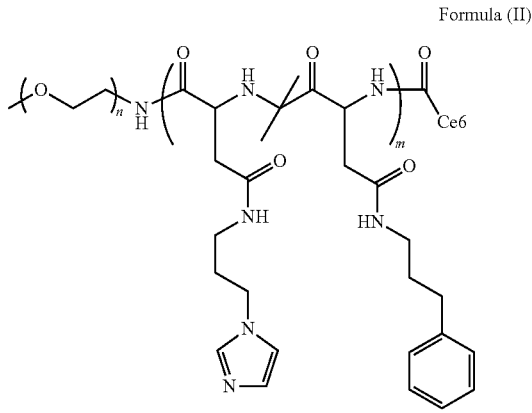

Formula (II)

wherein n and m are independently an integer of 5-500,
wherein at a pH range of 4-7.2, the ligand A is separated from the MRI contrasting agent and the surface charge of ligand B changes from negative to positive.

* * * * *